US009107792B2

(12) United States Patent
Catacchio et al.

(10) Patent No.: US 9,107,792 B2
(45) Date of Patent: Aug. 18, 2015

(54) CARRIAGE FOR A SURGICAL BOOT OF A HIP DISTRACTOR (71) Applicant: ALLEN MEDICAL SYSTEMS, INC., Batesville, IN (US)

(72) Inventors: Anthony V. Catacchio, Arlington, MA (US); Jesse S. Drake, Clinton, MA (US); Andrew D. Clark, Allston, MA (US); Frederick K. Newey, Pelham, NH (US); Sarah M. Steinberg, Somverville, MA (US); Dustin T. Libby, Belmont, MA (US)

(73) Assignee: Allen Medical Systems, Inc., Batesville, IN (US)

( * ) Notice: Subject to any disclaimer, the term of this patent is extended or adjusted under 35 U.S.C. 154(b) by 223 days.

(21) Appl. No.: 13/788,677

(22) Filed: Mar. 7, 2013

(65) Prior Publication Data

US 2014/0068866 A1   Mar. 13, 2014

Related U.S. Application Data (60) Provisional application No. 61/698,176, filed on Sep. 7, 2012.

(51) Int. Cl.
*A47C 20/00* (2006.01)
*A61G 13/12* (2006.01)
*A61G 13/00* (2006.01)
(Continued)

(52) U.S. Cl.
CPC ........ *A61G 13/1205* (2013.01); *A61G 13/0036* (2013.01); *A61G 13/101* (2013.01); *A61G 13/125* (2013.01); *A61G 13/1245* (2013.01); *A61F 5/042* (2013.01)

(58) Field of Classification Search
CPC ..... Y10T 16/18; Y10T 16/184; Y10T 16/205; Y10T 16/364; Y10T 16/384; E05D 15/063; A61G 13/12; A61G 13/1245; A61G 13/125; A61G 7/0755; A61G 13/101; A47C 20/021; A61B 6/0421; A61B 19/203
USPC ....... 5/630, 621, 624, 646–651, 81.1 R–87.1; 248/424, 429, 298.1
See application file for complete search history.

(56) References Cited

U.S. PATENT DOCUMENTS 1,160,451 A   11/1915 Sanford
1,501,120 A   7/1924  Karrer
(Continued)

OTHER PUBLICATIONS

Extended European Search Report for EP Application No. 13183409, dated May 8, 2014, 10 pages.
(Continued)

*Primary Examiner* — Timothy D Collins
*Assistant Examiner* — Richard G Davis
(74) *Attorney, Agent, or Firm* — Barnes & Thornburg LLP (57) ABSTRACT A carriage for a limb support includes a space for receiving a longitudinal member of a patient support apparatus, a plurality of rollers configured to engage the longitudinal member and a locking mechanism. The plurality of rollers is configured to maintain alignment of the carriage during movement of the carriage along the longitudinal member. The carriage also includes an elastomeric member that resists rotation to prevent unwanted motion of the carriage. The locking mechanism is configured to secure the carriage to the longitudinal member at any of an infinite number of positions along the length of the longitudinal member, the locking mechanism being lockable with a single action.

18 Claims, 5 Drawing Sheets

(51) Int. Cl.
*A61G 13/10* (2006.01)
*A61F 5/042* (2006.01)

(56) References Cited

U.S. PATENT DOCUMENTS

| | | | |
|---|---|---|---|
| 3,509,876 A | 5/1970 | Pilz | |
| 3,654,920 A | 4/1972 | Staib | |
| 3,745,996 A | 7/1973 | Rush, Sr. | |
| 3,982,742 A | 9/1976 | Ford | |
| 4,180,254 A | 12/1979 | Lee et al. | |
| 4,185,813 A | 1/1980 | Spann | |
| 4,252,306 A | 2/1981 | Johnson et al. | |
| 4,367,869 A | 1/1983 | Dailey et al. | |
| 4,372,452 A * | 2/1983 | McCord | 212/285 |
| 4,373,709 A | 2/1983 | Whitt | |
| 4,407,277 A | 10/1983 | Ellison | |
| 4,418,900 A | 12/1983 | Ricke | |
| 4,428,571 A | 1/1984 | Sugarman | |
| 4,443,005 A | 4/1984 | Sugarman et al. | |
| 4,471,952 A | 9/1984 | Spann | |
| 4,482,138 A | 11/1984 | Spann | |
| 4,526,355 A | 7/1985 | Moore et al. | |
| 4,545,573 A | 10/1985 | Murphy | |
| 4,579,324 A | 4/1986 | McConnell | |
| 4,620,698 A | 11/1986 | Reed et al. | |
| 4,681,309 A | 7/1987 | Lechner | |
| 4,702,465 A | 10/1987 | McConnell | |
| 4,732,145 A | 3/1988 | Latham | |
| 4,766,892 A | 8/1988 | Kreitman | |
| 4,782,827 A | 11/1988 | Paratte | |
| 4,802,464 A | 2/1989 | Deprez | |
| 4,809,687 A | 3/1989 | Allen | |
| 4,827,496 A | 5/1989 | Cheney | |
| 4,872,656 A | 10/1989 | Brendgord et al. | |
| 4,877,206 A * | 10/1989 | Barrett | 248/49 |
| 4,886,258 A | 12/1989 | Scott | |
| 4,913,413 A | 4/1990 | Raab | |
| 4,940,218 A | 7/1990 | Akcelrod | |
| 5,001,739 A | 3/1991 | Fischer | |
| 5,015,251 A | 5/1991 | Cherubini | |
| 5,025,802 A | 6/1991 | Laico et al. | |
| 5,027,799 A | 7/1991 | Laico et al. | |
| 5,042,508 A | 8/1991 | Richard | |
| 5,052,378 A | 10/1991 | Chitwood | |
| 5,056,535 A | 10/1991 | Bonnell | |
| 5,097,847 A | 3/1992 | Mikhail et al. | |
| D336,898 S | 6/1993 | Cherubini et al. | |
| 5,290,220 A | 3/1994 | Guhl | |
| 5,369,827 A | 12/1994 | Parke et al. | |
| 5,462,551 A | 10/1995 | Bailey et al. | |
| 5,511,255 A | 4/1996 | Schuerch | |
| 5,514,143 A | 5/1996 | Bonutti et al. | |
| 5,515,562 A | 5/1996 | Miller et al. | |
| 5,549,707 A | 8/1996 | Weaver | |
| 5,582,379 A | 12/1996 | Keselman et al. | |
| 5,608,934 A | 3/1997 | Torrie et al. | |
| 5,645,079 A | 7/1997 | Zahiri et al. | |
| 5,658,315 A | 8/1997 | Lamb et al. | |
| 5,799,349 A | 9/1998 | Petersen | |
| 5,802,641 A | 9/1998 | Van Steenburg | |
| 5,806,117 A | 9/1998 | Gotfried | |
| 5,882,280 A | 3/1999 | Dahlin, Jr. | |
| 5,918,330 A | 7/1999 | Navarro et al. | |
| 5,961,085 A | 10/1999 | Navarro et al. | |
| 6,012,456 A | 1/2000 | Schuerch | |
| 6,017,006 A | 1/2000 | Cherubini et al. | |
| 6,058,534 A | 5/2000 | Navarro et al. | |
| 6,263,531 B1 | 7/2001 | Navarro et al. | |
| 6,277,141 B1 | 8/2001 | Lake | |
| 6,289,537 B1 | 9/2001 | Hopper et al. | |
| 6,295,671 B1 | 10/2001 | Reesby et al. | |
| 6,295,672 B1 | 10/2001 | Vassallo, Jr. | |
| 6,306,146 B1 | 10/2001 | Dinkler | |
| 6,378,149 B1 | 4/2002 | Sanders et al. | |
| 6,438,777 B1 | 8/2002 | Bender | |
| 6,491,273 B2 | 12/2002 | King et al. | |
| 6,557,195 B2 | 5/2003 | Dinkler | |
| 6,698,044 B2 | 3/2004 | Limpert et al. | |
| 6,704,959 B2 | 3/2004 | Schuerch | |
| 6,723,036 B2 | 4/2004 | Weaver et al. | |
| 6,804,846 B2 | 10/2004 | Schuerch | |
| 6,813,788 B2 | 11/2004 | Dinkler et al. | |
| 6,826,794 B2 | 12/2004 | Mahoney et al. | |
| 6,869,194 B2 | 3/2005 | Weaver et al. | |
| 7,026,940 B2 | 4/2006 | Cherubini | |
| 7,082,631 B2 | 8/2006 | Czop | |
| 7,175,900 B2 | 2/2007 | Schaefer | |
| 7,243,654 B2 | 7/2007 | Schuerch | |
| 7,294,114 B1 | 11/2007 | Clement et al. | |
| 7,311,441 B2 | 12/2007 | Weaver et al. | |
| 7,316,040 B2 | 1/2008 | Siccardi et al. | |
| 7,334,276 B2 | 2/2008 | Pfeuffer et al. | |
| 7,407,309 B2 | 8/2008 | Scholz | |
| 7,412,311 B2 | 8/2008 | Georgi et al. | |
| 7,454,806 B2 | 11/2008 | Koch et al. | |
| 7,458,117 B2 | 12/2008 | Schaefer | |
| 7,465,065 B2 | 12/2008 | Marka | |
| 7,497,006 B2 | 3/2009 | Davis et al. | |
| 7,507,244 B2 | 3/2009 | Dinkler | |
| 7,513,645 B2 | 4/2009 | Marka et al. | |
| 7,517,347 B2 | 4/2009 | Hug et al. | |
| 7,520,004 B2 | 4/2009 | Czop | |
| 7,534,270 B2 | 5/2009 | Ball | |
| 7,544,007 B2 | 6/2009 | Easton | |
| 7,552,492 B2 | 6/2009 | Rolfes et al. | |
| D602,162 S | 10/2009 | Albrecht et al. | |
| D604,421 S | 11/2009 | Albrecht et al. | |
| D604,422 S | 11/2009 | Albrecht et al. | |
| 7,611,460 B2 | 11/2009 | Dobrovolny | |
| 7,614,763 B2 | 11/2009 | Leibinger et al. | |
| D606,832 S | 12/2009 | Wan et al. | |
| 7,624,958 B2 | 12/2009 | Ropertz et al. | |
| 7,669,258 B2 | 3/2010 | Koch | |
| 7,669,261 B2 | 3/2010 | Fruh et al. | |
| 7,730,563 B1 | 6/2010 | Sklar et al. | |
| 7,731,141 B2 | 6/2010 | Schuerch | |
| 7,739,762 B2 | 6/2010 | Lamb et al. | |
| 7,746,009 B2 | 6/2010 | Held et al. | |
| 7,757,316 B2 | 7/2010 | Koch | |
| 7,784,126 B2 | 8/2010 | Meissner et al. | |
| 7,810,185 B2 | 10/2010 | Burstner et al. | |
| 7,818,839 B2 | 10/2010 | Koch et al. | |
| 7,832,401 B2 | 11/2010 | Torrie et al. | |
| 7,836,529 B2 | 11/2010 | Cherubini et al. | |
| 7,841,731 B2 | 11/2010 | Marka et al. | |
| 7,861,720 B1 | 1/2011 | Wolcott | |
| 7,865,985 B2 | 1/2011 | Revenus | |
| 7,870,624 B1 | 1/2011 | Winston | |
| D631,970 S | 2/2011 | Held | |
| 7,896,569 B2 | 3/2011 | Katzenstein | |
| 8,650,675 B2 * | 2/2014 | Imhoff | 5/85.1 |
| 2002/0012566 A1 | 1/2002 | Auchinleck et al. | |
| 2003/0028967 A1 | 2/2003 | Schuerch | |
| 2003/0172460 A1 | 9/2003 | Schuerch | |
| 2004/0030243 A1 | 2/2004 | Warschewske et al. | |
| 2005/0043610 A1 | 2/2005 | Warschewske et al. | |
| 2005/0088763 A1 | 4/2005 | Weaver et al. | |
| 2006/0225743 A1 | 10/2006 | Schuerch | |
| 2006/0229500 A1 | 10/2006 | Schuerch | |
| 2006/0261571 A1 * | 11/2006 | Mitchell | 280/250.1 |
| 2007/0015960 A1 | 1/2007 | Gornert et al. | |
| 2007/0265635 A1 * | 11/2007 | Torrie et al. | 606/105 |
| 2007/0272808 A1 | 11/2007 | Schuerch | |
| 2008/0134435 A1 | 6/2008 | Stolze et al. | |
| 2008/0163427 A1 | 7/2008 | Howe | |
| 2009/0026901 A1 | 1/2009 | Nies, III et al. | |
| 2009/0040366 A1 | 2/2009 | Voelker | |
| 2009/0067963 A1 | 3/2009 | Olszewski | |
| 2009/0080190 A1 | 3/2009 | Bauer et al. | |
| 2009/0085408 A1 | 4/2009 | Bruhn | |
| 2009/0085765 A1 | 4/2009 | Bruhn | |
| 2009/0122536 A1 | 5/2009 | Scholz | |
| 2009/0126112 A1 | 5/2009 | Kuchenbecker et al. | |
| 2009/0126115 A1 | 5/2009 | Doering et al. | |

(56) References Cited

U.S. PATENT DOCUMENTS

| | | |
|---|---|---|
| 2009/0127433 A1 | 5/2009 | Rosenheimer et al. |
| 2009/0141853 A1 | 6/2009 | Crews |
| 2009/0187081 A1 | 7/2009 | Kelly |
| 2009/0201632 A1 | 8/2009 | Bauer et al. |
| 2009/0213596 A1 | 8/2009 | Gull et al. |
| 2009/0227928 A1 | 9/2009 | Drake et al. |
| 2009/0231179 A1 | 9/2009 | Bruhn |
| 2009/0231853 A1 | 9/2009 | Scholz et al. |
| 2009/0236484 A1 | 9/2009 | Koch et al. |
| 2009/0241128 A1 | 9/2009 | Curbera et al. |
| 2009/0250073 A1 | 10/2009 | Alfery et al. |
| 2009/0316394 A1 | 12/2009 | Fritze et al. |
| 2009/0318770 A1 | 12/2009 | Marka et al. |
| 2009/0318771 A1 | 12/2009 | Marka et al. |
| 2009/0318772 A1 | 12/2009 | Marka et al. |
| 2009/0321604 A1 | 12/2009 | Revenus |
| 2010/0031446 A1 | 2/2010 | Wyslucha |
| 2010/0053982 A1 | 3/2010 | Klaus et al. |
| 2010/0081887 A1 | 4/2010 | Marka et al. |
| 2010/0107340 A1 | 5/2010 | Koch et al. |
| 2010/0230567 A1 | 9/2010 | Schuerch |
| 2010/0242177 A1 | 9/2010 | Malcolm et al. |
| 2010/0242181 A1 | 9/2010 | Bochner et al. |
| 2010/0249780 A1 | 9/2010 | Rolfes |
| 2010/0263124 A1 | 10/2010 | Marugg |
| 2010/0284731 A1 | 11/2010 | Bauer et al. |
| 2010/0319713 A1 | 12/2010 | Byers et al. |
| 2011/0023893 A1 | 2/2011 | Striggow et al. |
| 2011/0146528 A1* | 6/2011 | Schilke et al. .............. 104/53 |
| 2011/0190676 A1 | 8/2011 | Torrie et al. |
| 2012/0291197 A1* | 11/2012 | Martin et al. ............. 5/85.1 |
| 2013/0191995 A1* | 8/2013 | Bellows et al. ............ 5/624 |

OTHER PUBLICATIONS

Partial European Search Report for EP Application No. 13183409, dated Jan. 7, 2014, 6 pages.

* cited by examiner

CARRIAGE FOR A SURGICAL BOOT OF A HIP DISTRACTOR

CROSS REFERENCE TO RELATED APPLICATIONS

This application claims priority under 35 U.S.C. §119(e) to U.S. Provisional Application No. 61/698,176, filed Sep. 7, 2012 which is hereby expressly incorporated by reference herein.

BACKGROUND

This application claims priority under 35 U.S.C. §119(e) to U.S. Provisional Application Ser. No. 61/698,176 Filed Sep. 7, 2012, which is expressly incorporated by reference herein.

The present disclosure is related to a support apparatus for supporting a patient. More particularly, the present disclosure relates to a support apparatus including a surgical table and a limb support coupled to the surgical table.

Often, when a patient is sedated for a surgery, the patient is supported by and secured to braces or supports coupled to a surgical table. Sometimes, unique supports are provided for a patient's extremities such as arm boards, leg supports, hand boards, stirrups, and boots.

Supports known in the art sometimes secure patients to resist patient movement. Such supports can sometimes allow excessive patient movement relative to the supports. The position and orientation of supports is often adjusted during surgery to improve access to a surgical site or to move portions of the patient's body such as bones, muscles, tendons, and ligaments to evaluate the surgical results.

SUMMARY

The present application discloses one or more of the features recited in the appended claims and/or the following features which, alone or in any combination, may comprise patentable subject matter:

According to a first aspect of the present disclosure, a limb support comprises a longitudinal member configured to be coupled to a patient support apparatus, and a carriage movable along the longitudinal member to a plurality of positions. The carriage includes a plurality of rollers supporting the carriage relative to the longitudinal member for movement along the longitudinal member. The carriage also includes a clamp for securing the carriage to the longitudinal member. The clamp includes a plurality of elastomeric blocks which deform under a load to secure the carriage to the longitudinal member.

In some embodiments, at least one elastomeric block is deformed by a cam. In some embodiments, the carriage includes a housing, and the at least one elastomeric block is supported on a plate that is pivotably coupled to the housing.

In some embodiments, the carriage includes an actuator that is movable between a first position wherein the at least one elastomeric block is subjected to a first load and a second position wherein the at least one elastomeric block is subjected to a second load. In the first position, the elastomeric block permits relative movement between the at least one elastomeric block in the longitudinal member. In the second position, the second load deforms the elastomeric block sufficiently to prevent movement between the at least one elastomeric block and the longitudinal member under normal operating conditions.

In some embodiments, at least one of the plurality of rollers includes a guide surface that engages a portion of the longitudinal member to prevent lateral movement of the carriage relative to the longitudinal member. The longitudinal member may include an upper surface and a lower surface. The plurality of rollers may include a first roller supporting the carriage relative to the upper surface of the longitudinal member and a second roller supporting the carriage relative to the lower surface of the longitudinal member.

In some embodiments, the longitudinal member further includes first and second lateral surfaces and wherein the first and second rollers are formed to include surfaces that engage the first and second lateral surfaces of the longitudinal member.

In some embodiments, the at least one of the plurality of rollers includes a tread configured to resist rolling to dampen movement of the carriage along the longitudinal member.

According to another aspect of the present disclosure, a carriage for a limb support comprises a space for receiving a longitudinal member of a patient support apparatus, a plurality of rollers configured to engage the longitudinal member and a locking mechanism. The plurality of rollers is configured to maintain alignment of the carriage during movement of the carriage along the longitudinal member. The locking mechanism is configured to secure the carriage to the longitudinal member at any of an infinite number of positions along the length of the longitudinal member, the locking mechanism being lockable with a single action.

In some embodiments, the locking mechanism includes a cam acting on a deformable block to engage the deformable block with the longitudinal member to secure the carriage to the longitudinal member.

In some embodiments, the carriage further comprises a housing defining the space. The locking mechanism may include a plate pivotably coupled to the housing, a deformable block positioned between the plate in the space, the deformable block configured to engage the longitudinal member, a cam supported by the housing, and an actuator. The cam may be configured to engage the plate to cause the plate to pivot between an unlocked position and a locked position. The actuator may be movable between a first position wherein the locking mechanism is unlocked and a second position wherein the locking mechanism is locked.

According to another aspect of the present disclosure, a carriage for a limb support comprises a housing defining a space for receiving a longitudinal member of a patient support apparatus, a plurality of rollers supported from the housing. The plurality of rollers is configured to engage the longitudinal member of the patient support apparatus for movement of the carriage relative to the longitudinal member. The carriage also comprises means for resisting rotation of at least one of the rollers relative to the longitudinal member to dampen the movement of the carriage relative to the longitudinal member.

In some embodiments, the means for resisting rotation includes elastomeric material that engages at least one surface of the longitudinal member to resist movement relative to the longitudinal member.

In some embodiments, the means for resisting rotation includes an annular member supported on a roller, the annular member deformable under a load to resist rotation of the roller relative to the longitudinal member.

In some embodiments, the means for resisting rotation includes an elastomeric block that is deformable under a load, the elastomeric block configured to engage at least one surface of the longitudinal member to limit movement between the carriage and the longitudinal member.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figures 1, 2:
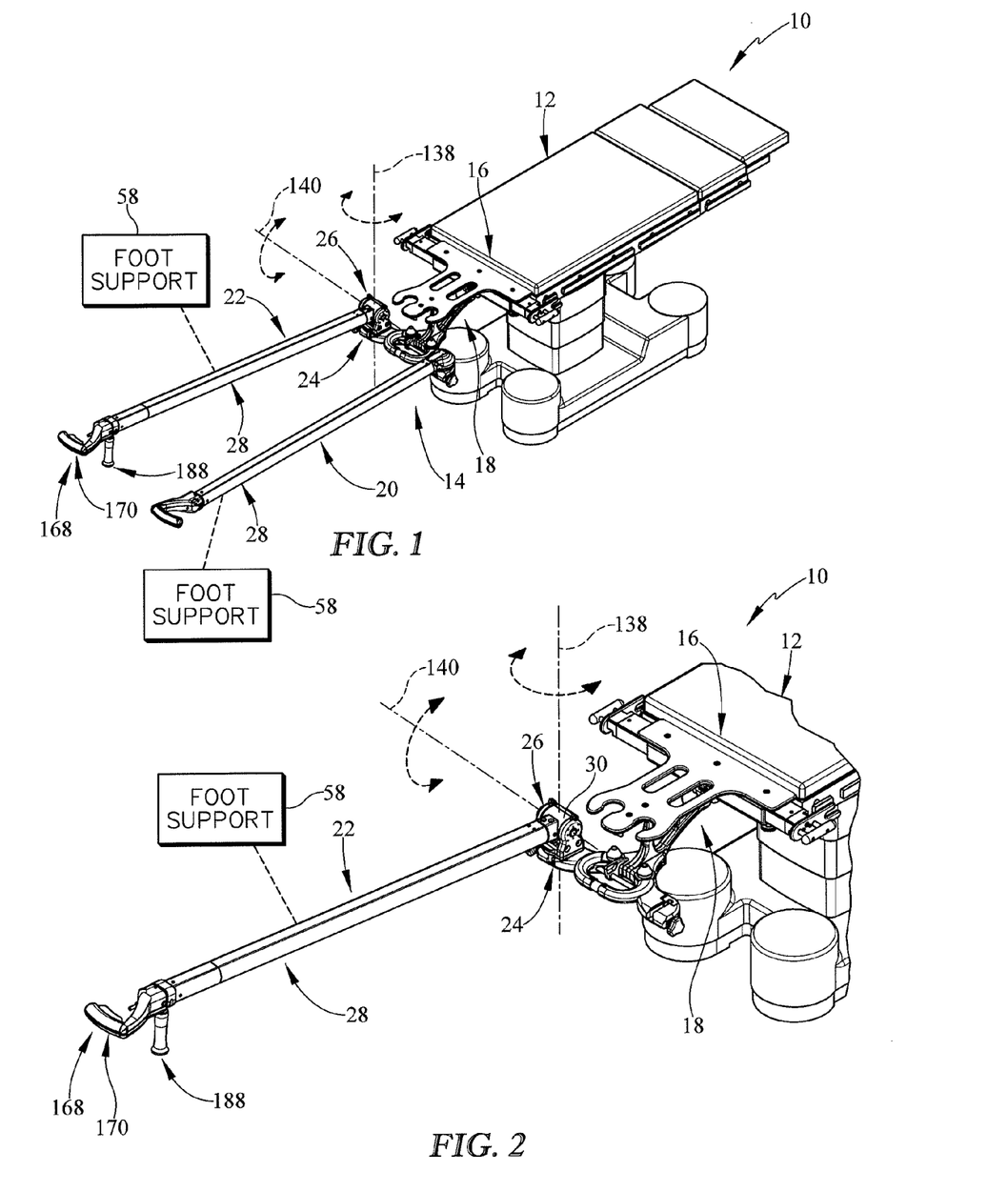
FIG. 1 is a perspective view of a patient support apparatus including a limb-support unit according to the present disclosure.
FIG. 2 is a perspective view similar to FIG. 1 with a portion of the limb-support unit omitted.

A support apparatus 10 includes, for example, a surgical table 12 and a limb-support unit 14 as shown in FIGS. 1-2. The limb-support unit 14 is coupled to a foot end 16 of the surgical table 12. In an example of use, the limb-support unit 14 supports a patient's legs and the surgical table 12 supports a patient's upper body. The limb-support unit 14 may be used to place tension on the patient's legs during surgery. This is also known as placing the patient's legs in traction. During a hip-replacement surgery, the patient's leg in which the hip is being replaced may need to be repositioned during the surgery to provide the surgeon with improved access while maintaining the patient's leg in traction. The limb-support unit 14 in accordance with the present disclosure provides the ability to reposition the patient's leg while maintaining that leg in traction.

Limb-support unit 14 includes a countertraction unit 18, a single-axis leg holder 20, and a two-axis leg holder 22 as shown in FIGS. 1-2. Both the leg holder 20 and the two-axis leg holder 22 each support a foot support 58. The countertraction unit 18 is coupled to the foot end 16 of the surgical table 12 in a fixed position as shown in FIGS. 1 and 2. The single-axis leg holder 20 is coupled to the countertraction unit 18 in a fixed position when supporting one of the patient's legs. When the single-axis leg holder 20 is not supporting one of the patient's legs, the single-axis leg holder 20 may be repositioned relative to the countertraction unit 18. The two-axis leg holder 22 is coupled in spaced-apart relation to the countertraction unit 18 as shown in FIGS. 1 and 2. Portions of the two-axis leg holder 22 move relative to the countertraction unit 18 as suggested in FIGS. 1 and 2.

Figure 3:
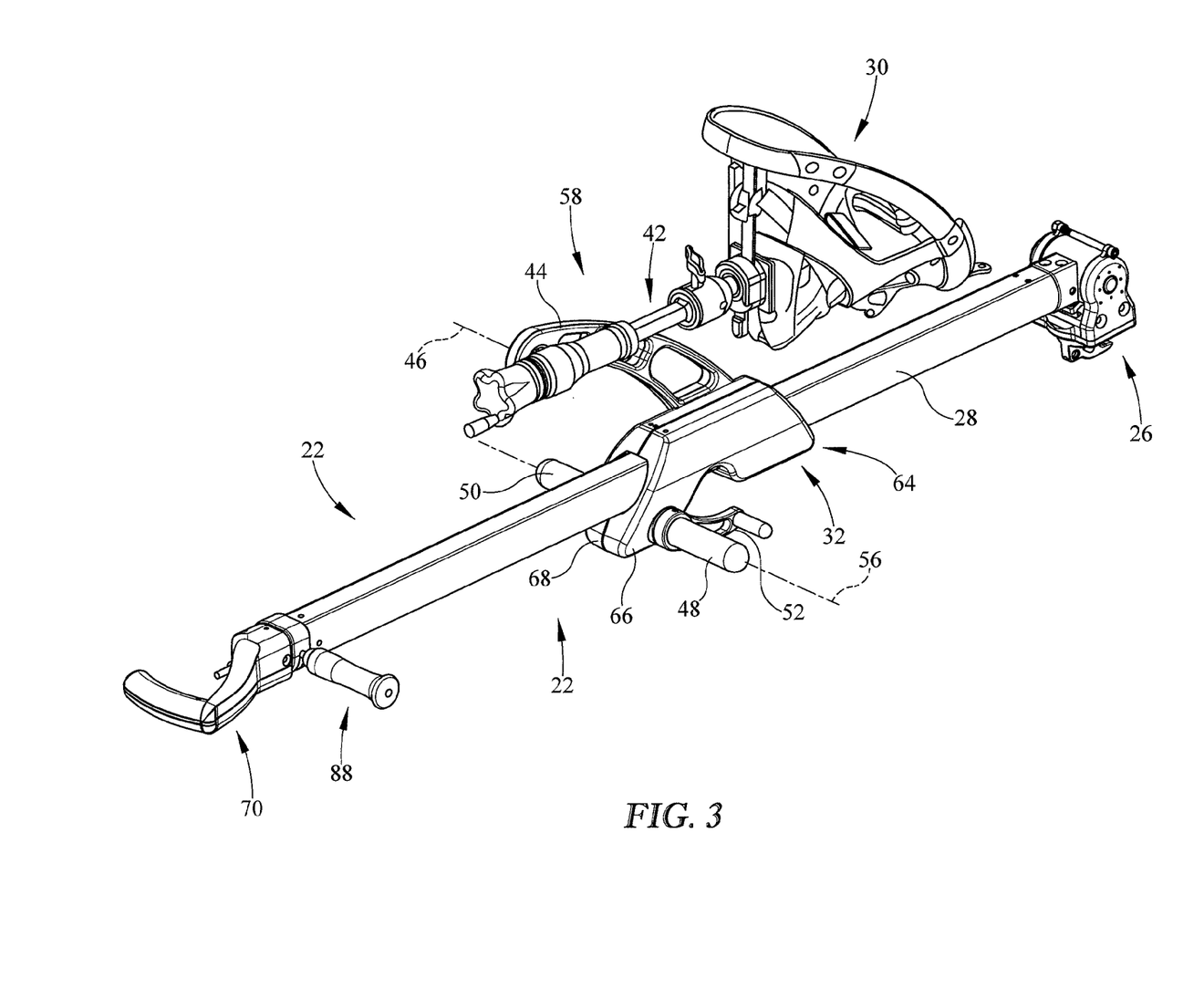
FIG. 3 is a perspective view of a foot support supported on a two-axis leg support, the foot support including a surgical boot supported from a carriage.
Figure 4:
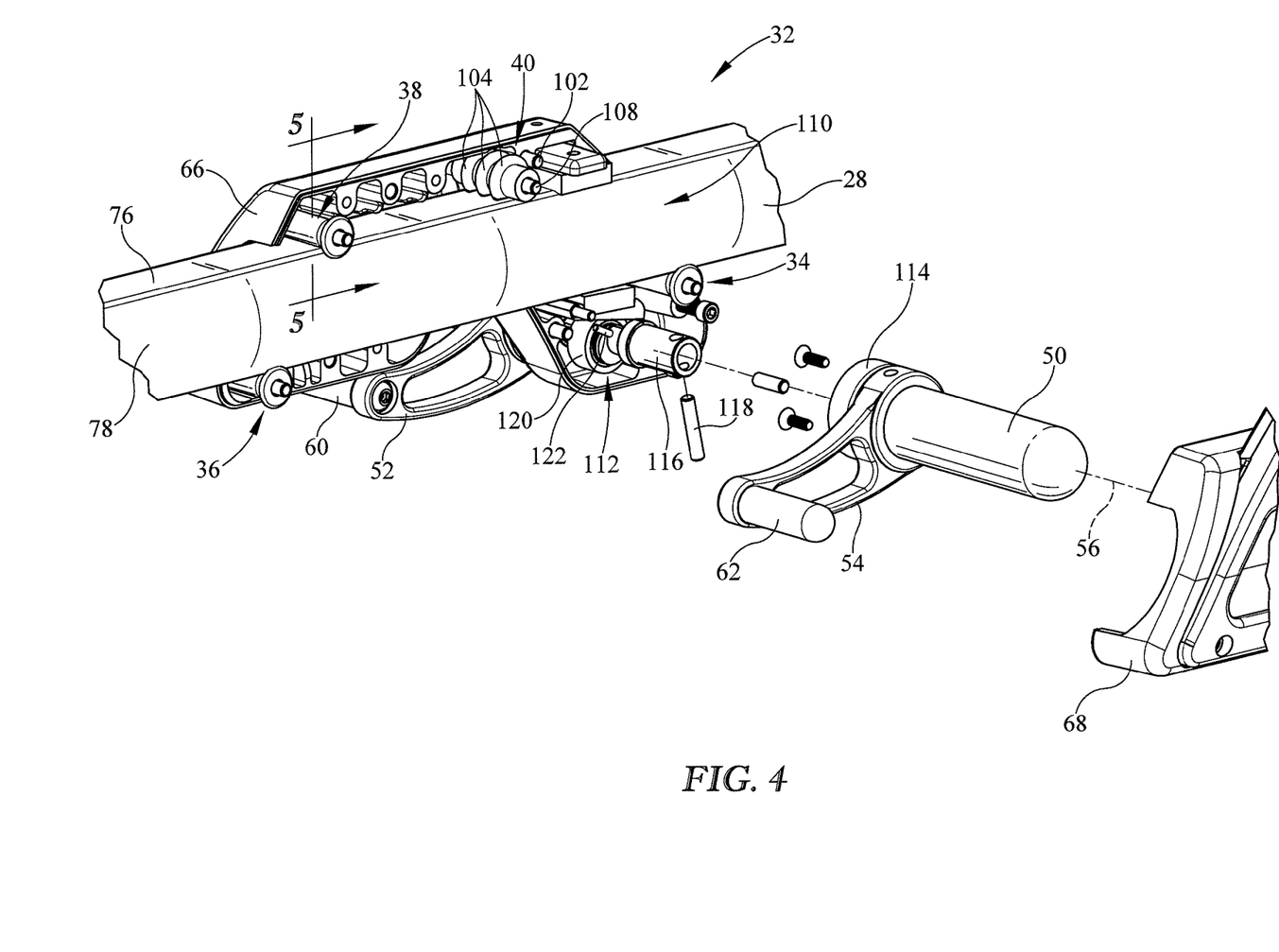
FIG. 4 is an exploded assembly view of the carriage of FIG. 3.

The two-axis leg holder 22 includes a joint mount 24, a multi-axis joint 26, and a spar 28, as shown in FIGS. 3 and 4. The joint mount 24 is coupled to the countertraction unit 18 in a fixed position while the limb-support unit 14 supports portions of the patient. When the limb-support unit 14 is not supporting portions of the patient, the joint mount 24 may be decoupled from the countertraction unit 18 and repositioned on the countertraction unit 18. The multi-axis joint 26 is arranged to interconnect the spar 28 and the joint mount 24 to cause the spar 28 to move relative to the joint mount 24 as suggested in FIG. 4. The spar 28 is coupled to the multi-axis joint 26 and arranged to extend away from the multi-axis joint 26 to support the patient's leg in traction during surgery.

Referring now to FIG. 3, the foot support 58 includes a surgical boot 30 supported on a carriage 32 that is positionable along the spars 28 of either single-axis leg holder 20 or two-axis leg holder 22. Boot 30 is supported from a coupler 42 which is adjustable to change the orientation of boot 30 relative to carriage 32. A suitable boot is disclosed in U.S. patent application Ser. No. 13/151,627 titled "SURGICAL FOOT SUPPORT WITH TIGHTENER SYSTEM," or U.S. patent application Ser. No. 13/151,617 titled "SURGICAL FOOT SUPPORT WITH HANDLES," the disclosures of which are each incorporated in their entirety by reference herein. Coupler 42 is pivotably coupled to a strut 44 of carriage 32 and pivotable about an axis 46. Carriage 32 includes a pair of handles 48, 50 which are usable by a caregiver to move the carriage 32 along the spar 28. A pair of actuators 52, 54 are movable about an axis 56 through the handles 48, 50. Actuator 52 includes a handle 60 and actuator 54 includes a handle 62. Handles 60, 62 are used to move the actuators 52, 54 between a released position shown in phantom in FIG. 6 and a locked position shown in phantom in FIG. 7. The carriage 32 also includes a housing 64 and has a first cover 66 and a second cover 68, the first cover 66 and second cover 68 coupleable together over the spar 28 to retain the carriage 32 on the spar 28.

Figure 5:
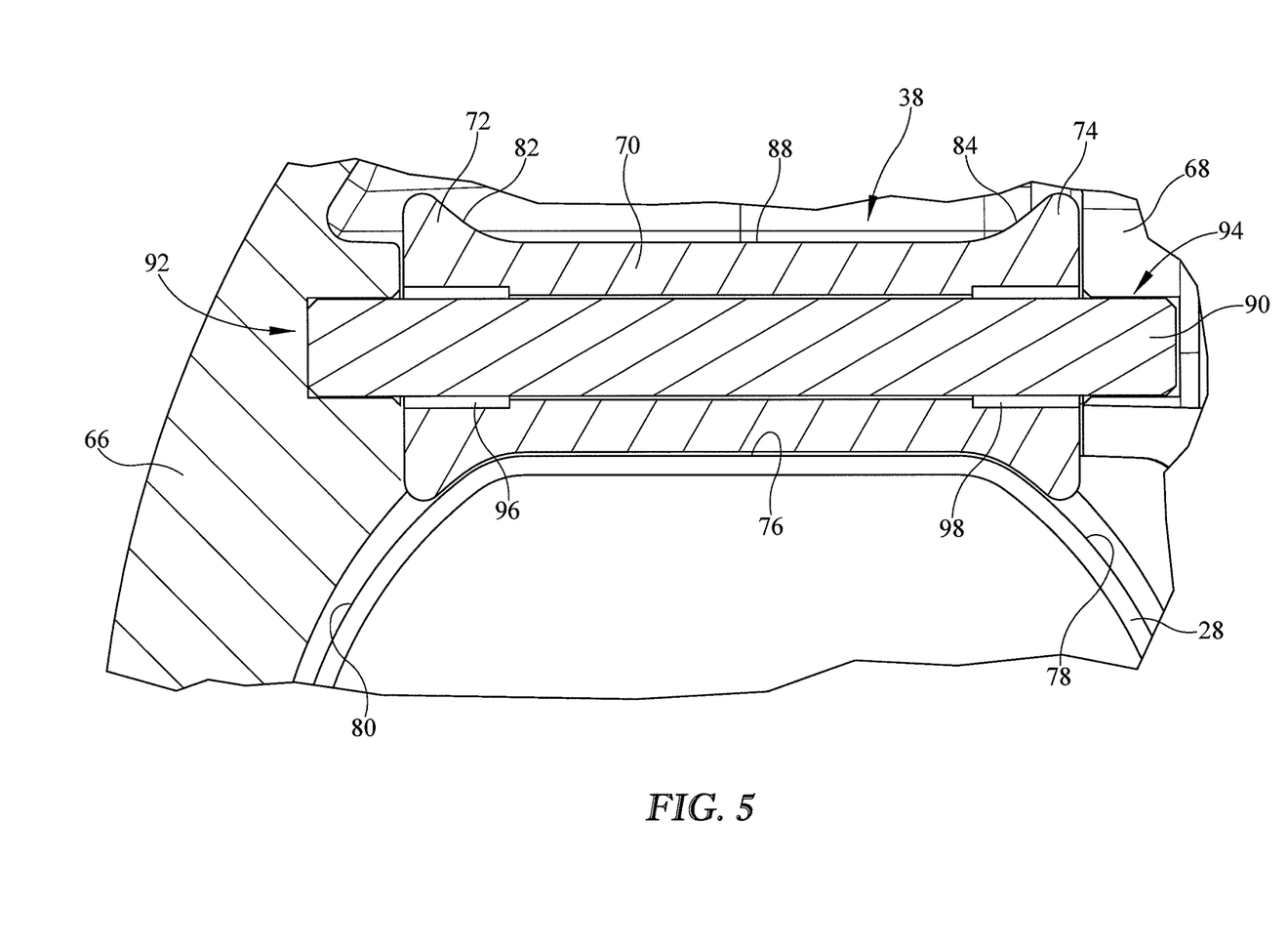
FIG. 5 is a cross-sectional view taken along line 5-5 of FIG. 4.

Referring now to FIG. 4, the carriage 32 includes four rollers 34, 36, 38, and 40 which engage the spar 28 to support the carriage 32 for movement along the spar 28. Each of the rollers 34, 36, and 38 have a cylindrical body 70 and expanded ends 72 and 74 as shown in FIG. 5 where roller 38 is shown in cross-section. The spar 28 includes an upper surface 76, and a lower surface 86, both of which are generally planar and parallel to each other. The spar 28 is formed to include a first side surface 78 and a second side surface 80 which are convex as shown in FIG. 5. A surface 88 of the cylindrical body 70 of roller 38 engages the upper surface 76 of spar 28. The expanded ends 72 and 74 of roller 38 define concave surfaces 82 and 84 respectively. When the roller 38 is engaged with the spar 28, the concave surface 82 engages the convex surface 80 and the concave surface 84 engages the convex surface 78 to guide the roller 38 along the spar 28 to prevent lateral movement of the carriage 32 relative to the spar 28. This prevents the carriage 32 from becoming misaligned during positioning of this foot support 58.

The roller 38 includes an axle 90 received at one end into a cavity 92 in cover 66 and into a cavity 94 in cover 68 at the opposite end of the axle 90. The roller body 70 is supported on the axle 90 by two bearings 96 and 98 such that the roller 38 rotates about the axle 90 when the carriage 32 is moved along the spar 28. The rollers 34 and 36 are supported in a similar manner from the covers 66 and 68. Because the rollers 34 and 36 are positioned below the spar 28, the outer surface 88 of the rollers 34 and 36 engage the lower surface 86 of the spar 28 as the carriage is moved along the spar 28.

The fourth roller 40 is different from the rollers 34, 36, and 38 in that roller 40 is configured to provide some resistance during movement of the carriage 32 along the spar 28. The need for rolling resistance of the carriage is created by the potential for the two-axis leg holder 22 to be rotated about an axis 140 shown in FIGS. 1-3. When the actuators 52 and 54 are in the released position of FIG. 6, the carriage 32 is free to move along the spar 28. A user may operate the controls 170, 188 at a distal end 168 of the two-axis leg holder 22 to release the two-axis leg holder 22 for movement about axis 140. Without the rolling resistance provided by the roller 40, the entire foot support 58 could move rapidly along the spar 28 unexpectedly causing damage to the foot support 58 or the two-axis leg holder 22. Referring now to FIG. 4, roller 40 includes a cylindrical body 102 supported on an axle 108. In addition, roller 40 includes three annular treads 104 that are supported on the cylindrical body 102. The annular treads 104 comprise a resilient elastomeric material that deforms under a load. The treads 104 are engaged with the cylindrical body 102 with a frictional interference that resists movement of the treads 104 relative to the cylindrical body 102. The cylindrical body 102 is supported by bearings (not shown) on the axle 108 similar to the structure of rollers 34, 36, and 38 so that the cylindrical body 102 rotates relative to the axle 108. The axle 108 is supported in the covers 66 and 68 in a manner similar to the rollers 34, 36, and 38. The treads 104 engage the upper surface 76 of the spar 28 as the carriage 32 is moved along the spar 28. Because the treads 104 deform under a load, they provide rolling resistance to movement of the carriage 32 along the spar 28. Illustratively, the treads 104 are O-rings.

Figure 6:
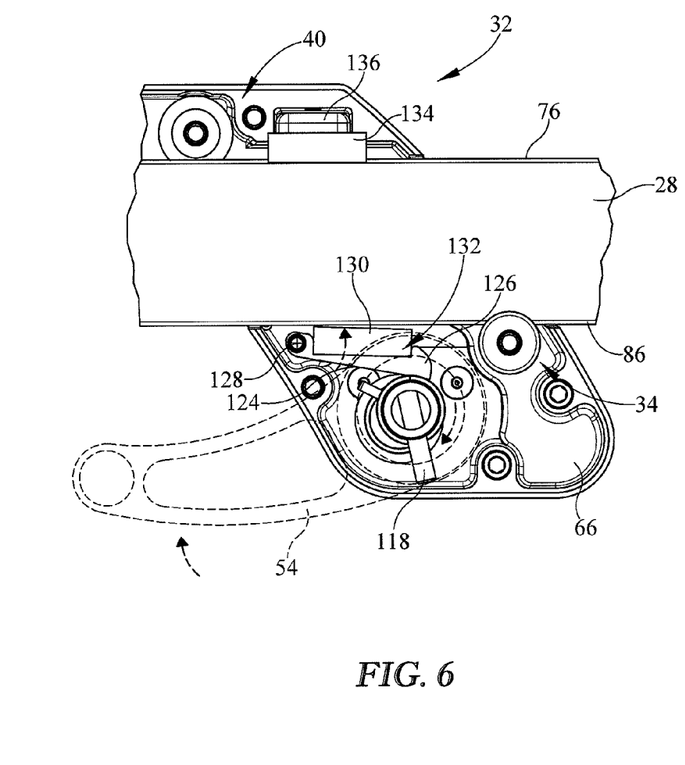
FIG. 6 is a side view of a portion of the carriage of FIG. 3 with portions removed, the carriage including a locking mechanism in an unlocked position.
Figures 7, 8:
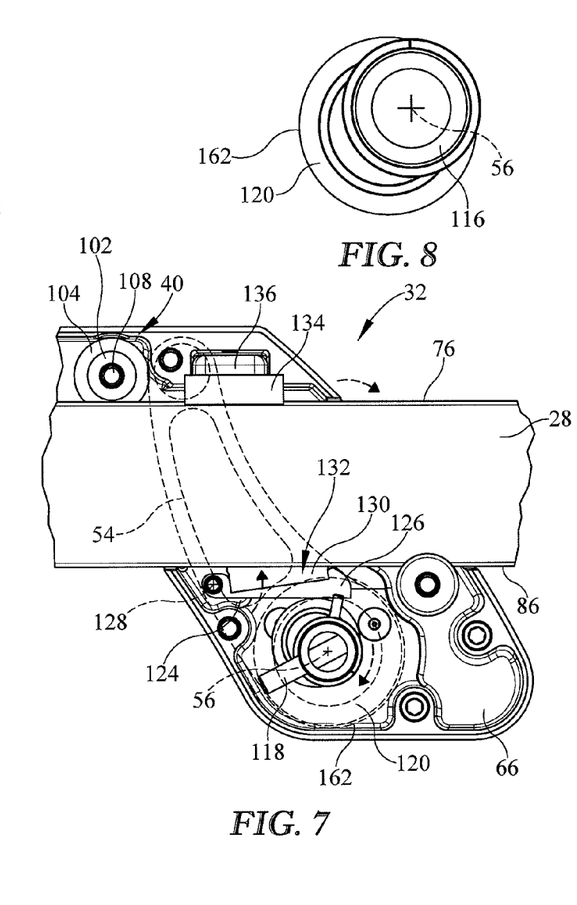
FIG. 7 is a view similar to FIG. 6 with the locking mechanism in a locked position.
FIG. 8 is a side view of a cam of the locking mechanism of FIGS. 6 and 7.

Referring again now to FIG. 4, the carriage 32 includes a locking mechanism 110 that includes the actuators 52, 54 which move between the released position of FIG. 6 and the locked position of FIG. 7. As shown in FIG. 4, actuator 54 is coupled to handle 50 such that they rotate about axis 56 together. Locking mechanism 110 includes a cam assembly 112 which is coupled to and supported from the handles 48 and 50. Handle 50 is fixed relative to the housing 64. A coupler 116 of cam assembly 112 is coupled to the actuator 54 and moves with the actuator 54. A pin 118 moves relative to a collar 114 such that the coupler 116 rotates with the actuator 54 about the axis 56. The collar 114 includes a motion limiting slot (not shown) that limits the movement of the cam assembly 112 about axis 56. The coupler 116 is secured to a cam 120. It should be understood that while not shown, the relationship between the actuator 52 and handle 48 with the cam assembly 112 is similar to that described herein and provides access for a user on the opposite side of the spar 28 from the handle 62 of actuator 54.

Referring now to FIGS. 6-8, the center of cam 120 is offset from the axis 56 so that rotation about the axis 56 causes eccentric motion such that the outer surface 162 of cam 120 acts on a lower surface 124 of a plate 126. Plate 126 is pivotably coupled to the housing 64 and pivotable about an axis 128. The action of the cam surface 162 on the lower surface 124 of the plate 126 urges the plate 126 upwardly. An elastomeric block 130 is positioned between the plate 126 and the lower surface 86 of the spar 28. In the released position shown in FIG. 6, the elastomeric block 130 is an slight engagement with the lower surface 86 of the spar 28 so that there is freedom of movement therebetween. In the locked position shown in FIG. 7, the plate 126 is urged upwardly, compressing the elastomeric block 130 between the plate 126 and the spar 28. The plate 126 is formed to include a tray 132 that retains the elastomeric block 130 and the bias of the elastomeric block 130 grips the spar 28 between elastomeric block 130 and a second elastomeric block 134 positioned to engage the upper surface 76 of the spar 28. The elastomeric block 134 is secured to a coupler 136 which floats in the housing 64 when the locking mechanism 110 is released. Movement of the locking mechanism 110 to the locked position of FIG. 7, causes a clamp force between the elastomeric blocks 130 and 134 in the spar 28 to prevent movement of the carriage 32 along the spar 28 under normal operating conditions. For example, the locking force is sufficient to prevent movement if a caregiver inadvertently bumps or leans on the foot support 58. The pin 118 and slot formed in collar 114 acts as a motion limiter and as a stop for the locking mechanism 110 so that the user can move the locking mechanism 110 between the unlocked and locked positions with a single action, the motion limiter cooperating with the cam 120 to define the locked position.

In use, a user will secure the foot of a patient into the surgical boot 30, adjust the position of the two-axis leg holder 22 or the single-axis leg holder 20, position the carriage 32 in the correct location along the spar 28 and move the locking mechanism 110 to the locked position, and further adjust the position of the patient's foot using adjustments available on the coupler 42. The carriage 32 provides the benefit of allowing the position of the foot support 58 to be positioned in an infinite number of positions along the length of the spar 28 and to be locked into position with a single action to position locking mechanism 110.

Although certain illustrative embodiments have been described in detail above, variations and modifications exist within the scope and spirit of this disclosure as described and as defined in the following claims.

The invention claimed is:

1. A limb support comprising
   a longitudinal member configured to be coupled to a patient support apparatus, and
   a carriage movable along the longitudinal member to a plurality of positions, the carriage including a plurality of rollers supporting the carriage relative to the longitudinal member for movement along the longitudinal member, and a clamp for securing the carriage to the longitudinal member, the clamp including a plurality of elastomeric blocks which deform under a load to secure the carriage to the longitudinal member; wherein at least one of the plurality of rollers of the limb support includes a tread configured to resist rolling to dampen movement of the carriage along the longitudinal member.

2. The limb support of claim 1, wherein at least one elastomeric block is deformed by a cam.

3. The limb support of claim 2, wherein the carriage includes a housing, and the at least one elastomeric block is supported on a plate that is pivotably coupled to the housing.

4. The limb support of claim 3, wherein the carriage includes an actuator that is movable between a first position wherein the at least one elastomeric block is subjected to a first load which permits relative movement between the at least one elastomeric block and the longitudinal member and a second position wherein the at least one elastomeric block is subjected to a second load which deforms the elastomeric block sufficiently to prevent movement between the at least one elastomeric block and the longitudinal member under normal operating conditions.

5. The limb support of claim 2, wherein at least one of the plurality of rollers includes a guide surface that engages a portion of the longitudinal member to prevent lateral movement of the carriage relative to the longitudinal member.

6. The limb support of claim 1, wherein at least one of the plurality of rollers includes a guide surface that engages a portion of the longitudinal member to prevent lateral movement of the carriage relative to the longitudinal member.

7. The limb support of claim 6, wherein the longitudinal member includes an upper surface and a lower surface and wherein the plurality of rollers includes a first roller supporting the carriage relative to the upper surface of the longitudinal member and a second roller supporting the carriage relative to the lower surface of the longitudinal member.

8. The limb support of claim 7, wherein the longitudinal member further includes first and second lateral surfaces and wherein the first and second rollers are formed to include surfaces that engage the first and second lateral surfaces of the longitudinal member.

9. The limb support of claim 8, wherein at least one of the plurality of rollers includes a guide surface that engages a portion of the longitudinal member to prevent lateral movement of the carriage relative to the longitudinal member.

10. A carriage for a limb support comprising
a space for receiving a longitudinal member of a patient support apparatus,
a plurality of rollers configured to engage the longitudinal member, the plurality of rollers configured to maintain alignment of the carriage during movement of the carriage along the longitudinal member, wherein
at least one of the plurality of rollers includes a tread configured to resist rolling to dampen movement of the carriage along the longitudinal member,
a locking mechanism configured to secure the carriage to the longitudinal member at any of an infinite number of positions along the length of the longitudinal member, the locking mechanism being lockable with a single action.

11. The carriage of claim 10, wherein the locking mechanism includes a cam acting on a deformable block to engage the deformable block with the longitudinal member to secure the carriage to the longitudinal member.

12. The carriage of claim 10, wherein the carriage further comprises a housing defining the space, the locking mechanism including a plate pivotably coupled to the housing, a deformable block supported on the plate in the space, the deformable block configured to engage the longitudinal member, a cam supported from the housing, the cam configured to engage the plate to cause the plate to pivot between an unlocked position and a locked position, and an actuator movable between a first position wherein the locking mechanism is unlocked and a second position wherein the locking mechanism is locked.

13. The limb support of claim 10, wherein at least one of the plurality of rollers includes a guide surface configured to engage a portion of the longitudinal member to prevent lateral movement of the carriage relative to the longitudinal member.

14. A carriage for a limb support comprising
a housing defining a space for receiving a longitudinal member of a patient support apparatus, and
a plurality of rollers supported from the housing and configured to engage the longitudinal member of the patient support apparatus for movement of the carriage relative to the longitudinal member, wherein
at least one of the plurality of rollers includes a tread configured to resist rolling to dampen movement of the carriage along the longitudinal member.

15. The carriage of claim 14, wherein the tread includes elastomeric material that engages at least one surface of the longitudinal member to resist movement relative to the longitudinal member.

16. The carriage of claim 14, wherein the tread includes an annular member supported on a roller, the annular member deformable under a load to resist rotation of the roller relative to the longitudinal member.

17. The carriage of claim 14, wherein the carriage includes an elastomeric block that is deformable under a load, the elastomeric block configured to engage at least one surface of the longitudinal member to limit movement between the carriage and the longitudinal member.

18. The limb support of claim 14, wherein at least one of the plurality of rollers includes a guide surface configured to engage a portion of the longitudinal member to prevent lateral movement of the carriage relative to the longitudinal member.

* * * * *